(12) United States Patent
Sowerby et al.

(10) Patent No.: US 6,362,477 B1
(45) Date of Patent: Mar. 26, 2002

(54) BULK MATERIAL ANALYSER FOR ON-CONVEYOR BELT ANALYSIS

(75) Inventors: Brian Sowerby, Karella; Cheryl Lim, Peakhurst; James Tickner, Erskineville, all of (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/581,160

(22) PCT Filed: Dec. 10, 1998

(86) PCT No.: PCT/AU98/01026

§ 371 Date: Jul. 14, 2000

§ 102(e) Date: Jul. 14, 2000

(87) PCT Pub. No.: WO99/30139

PCT Pub. Date: Jun. 17, 1999

(30) Foreign Application Priority Data

Dec. 10, 1997 (AU) .............................. PP 0830

(51) Int. Cl.$^7$ .......................................... G01N 23/222
(52) U.S. Cl. ................. 250/358.1; 250/359.1; 250/252.1
(58) Field of Search ............ 250/358.1, 359.1, 250/370.06, 390.04, 394, 252.1; 376/159

(56) References Cited

U.S. PATENT DOCUMENTS

| | | | |
|---|---|---|---|
| 4,090,074 A | 5/1978 | Watt et al. ................. 250/273 |
| 4,682,043 A | 7/1987 | Marshall .................... 250/358 |
| 5,732,115 A | * 3/1998 | Atwell et al. ............... 376/159 |
| 5,825,030 A | 10/1998 | Hurwitz et al. ............. 250/358 |

FOREIGN PATENT DOCUMENTS

| | | |
|---|---|---|
| AU | 83431/82 | 11/1982 |
| DE | 217030 A1 | 1/1985 |

* cited by examiner

Primary Examiner—Scott J. Sugarman
Assistant Examiner—Richard Hanig
(74) Attorney, Agent, or Firm—Jacobson Holman, PLLC

(57) ABSTRACT

The present invention related generally to bulk material analyzers suitable for the direct on-line analysis of materials such as coal and minerals. It is targeted particularly at direct on-conveyor belt analysis. It includes: a shielded enclosure defining an analysis zone within it and having a passageway through it to allow transport of bulk material through the analysis zone. At least one neutron source (1,4) and at least two gamma ray detectors (3,5) are disposed within the enclosure to measure gamma-rays produced in the bulk material by both the neutron inelastic scatter and thermal neutron capture processes. A neutron source and a gamma-ray detector are arranged in either a transmission or backscatter geometry. A second gamma-ray detector is arranged either in a transmission or backscatter geometry with or without using a second neutron source. The arrangement of detectors is such that the bias in the spatial response of each, that is caused by the relative attenuation of neutrons and gamma-rays in the bulk material, at least partly compensates for bias in the spatial response of the other.

21 Claims, 7 Drawing Sheets

BULK MATERIAL ANALYSER FOR ON-CONVEYOR BELT ANALYSIS

TECHNICAL FIELD

The present invention relates generally to bulk material analysers suitable for the direct on-line analysis of materials such as coal and minerals. It is targeted particularly at direct on-conveyor belt analysis.

BACKGROUND ART

A key requirement for direct on-conveyor belt analysis is the ability to measure parameters of interest, such as elemental composition, independently of both horizontal and vertical segregation and independently of changes in belt loading.

Both neutron inelastic scatter (NIS) and thermal neutron capture (TNC) gamma-ray techniques have the advantages of using highly penetrating radiation so that measurements are averaged over a large volume of material on a conveyor belt. They are also capable of the simultaneous quantitative determination of many elements.

Thermal Neutron Capture (TNC) Gamma-Rays

The most widely used technique for on-line bulk material analysis is that based on thermal neutron capture (TNC) gamma-rays (sometimes referred to as the prompt gamma neutron activation analysis (PGNAA) technique). The TNC technique involves bombarding a bulk sample with neutrons from a radioisotope source, usually 252Cf. The 252Cf neutrons (average energy 2.3 MeV) are slowed down to thermal energies (about 0.025 eV) by collisions either in the sample or in an external moderator and then captured by the nuclei of elements present in the sample. The capture process in most cases is accompanied by the immediate release of energetic gamma-rays which are characteristic of the element. In most materials the capture gamma-rays form a complex spectrum of energies, which is capable of interpretation to provide analytical information on the proportion of the various elements present in the sample.

In previous applications of the TNC technique to on-conveyor belt analysis, spatial uniformity is controlled by the use of multiple sources and detectors in transmission geometry together with neutron moderators external to the sample. These external moderators are used to control the thermal neutron flux distribution in the sample to produce a more uniform spatial sensitivity.

In another development, an on-belt analyser has been described which comprises a 14 MeV pulsed neutron generator and a gamma-ray detector located on opposite sides of a conveyor belt. The neutrons are slowed down to thermal energies using heavy metal and polyethylene shields and TNC gamma-ray spectra are measured. However, the problem of spatial sensitivity is not addressed as it is assumed that the material is homogeneous and of constant profile on the belt.

Neutron Inelastic Scatter (NIS) Gamma-Rays

In the NIS technique, fast neutrons undergo direct inelastic scatter reactions with the nuclei of elements in a sample resulting in the production of prompt gamma-rays which are characteristic of the elements present. For NIS to occur the energy of the incident neutrons must be greater than the energy of the gamma-rays. Suitable high-energy neutron sources are 241 Am-Be (average neutron energy about 4.5 MeV), fast neutron generators (neutron energy 2.45 or 14 MeV) and 252Cf (average neutron energy 2.35 MeV). Generally higher energy neutron sources are better suited to NIS applications.

NIS and TNC are in many ways complementary since an element that may not be sensitive to NIS may be highly sensitive to TNC and vice versa. For example, carbon is easily determined using NIS but is only weakly excited in TNC; on the other hand, hydrogen is readily determined using TNC but it produces no NIS gamma-rays. By using a high-energy neutron source NIS is readily combined with TNC techniques to determine the concentration of most of the major elements in a wide range of samples. An example of a successful application combining NIS and TNC is the determination of carbon, hydrogen, ash and chlorine in low rank coal in a by-line geometry.

The NIS technique has been developed for a number of industrial applications on relatively homogeneous materials in sample by-lines. However applications to on conveyor belt analysis have not been attempted partly because of problems with spatial sensitivity of the technique. In a backscatter geometry the effective depth of penetration into the sample is limited. For the example of 4.43 MeV NIS carbon gamma-rays from coal using a 238 Pu—Be source, 50% of the measured gamma-rays originate in the first 50 mm of coal and 80% originate in the first 100 mm.

SUMMARY OF THE INVENTION

The invention is a bulk material analyser including: A shielded enclosure defining an analysis zone within it and having a passageway through it to allow transport of bulk material through the analysis zone. The shielded enclosure may be made of a material that contains a high hydrogen density, often combined with a material of high neutron capture cross section such as a compound of boron or lithium. The purpose of the shielded enclosure is to provide radiation shielding for personnel. In use, the bulk material is transported though the analysis zone on a conveyor belt or chute which passes along the passageway. At least one neutron source and at least two gamma-ray detectors are disposed within the enclosure to measure gamma-rays produced in the bulk material by both the NIS and TNC processes.

When one neutron source and a gamma-ray detector are arranged in a transmission or backscatter geometry, the spatial response of the gauge will be biased towards either the source side, the centre or the detector side of the sample, depending on the relative attenuation of neutrons and gamma-rays in the sample. The present invention provides a number of alternative methods to overcome this bias using a second detector or second source/detector configuration with a spatial response biased to compensate for the spatial bias of the first configuration. If the two configurations used are both transmission or both backscatter then two sources are required and the source (and detector) of the first configuration will be on the opposite side of the material to the source (and detector) of the second configuration. Variations on the above configurations involve multiple sources and/or detectors which are located across the passageway (perpendicular to the direction of travel) to improve spatial uniformity across the passageway.

Use of the invention can result in significant improvement in spatial uniformity, as a result of the use of two or more of the two possible source-sample-detector configurations, viz., backscatter or transmission configurations.

The neutron sources have sufficient energy to excite NIS gamma-rays from the element of interest; so called "fast neutron sources". Neutrons from these sources are also slowed to thermal energies in the sample and surroundings to produce TNC gamma-rays. Suitable sources include radioisotope sources and neutron generators of either continuous or pulsed mode. The neutron-induced gamma-ray measurements may be combined with separate measurements of gamma-ray transmission, thermal neutron flux or fast neutron flux, or any combination of them. NIS measurements may be combined with TNC measurements. Suitable high-energy neutron sources are 241Am—Be, a neutron generator or 252Cf, and suitable detectors are scintillation or solid state detectors such as thallium activated sodium iodide NaI(Tl), bismuth germanate BGO or hyperpure germanium.

BRIEF DESCRIPTION OF THE DRAWINGS

An example of the invention will now be described with reference to the accompanying drawings.

BEST MODES FOR CARRYING OUT THE INVENTION

Achievement of Spatial Insensitivity

An important property of a bulk-material analyser is that the measured composition should not depend on the spatial distribution of different elements within the sample. This is referred to as spatial insensitivity. The determination of the elemental composition of a sample relies on measuring the number of gamma-rays of characteristic energy reaching a suitable detector. This means that for a gauge exhibiting good spatial insensitivity, the probability of a gamma-ray being produced in a neutron interaction and surviving to reach a suitable detector should be constant within the sample volume.

The rate of production and subsequent detection of gamma-rays depends on the effective attenuation lengths of neutrons and gamma-rays in the sample and any surrounding material as well as the position of the sources and detectors with respect to the sample and each other. In a single source-single detector configuration, depending on the relative effective attenuation lengths of neutrons and gamma-rays in the sample, material nearest either the source side, the detector side or the centre of the sample will contribute excessively to the observed number of gamma-rays, thus biasing the composition measurement. Multiple transmission and/or backscattering source/detector configurations can be used to reduce or eliminate this bias.

Figure 1:
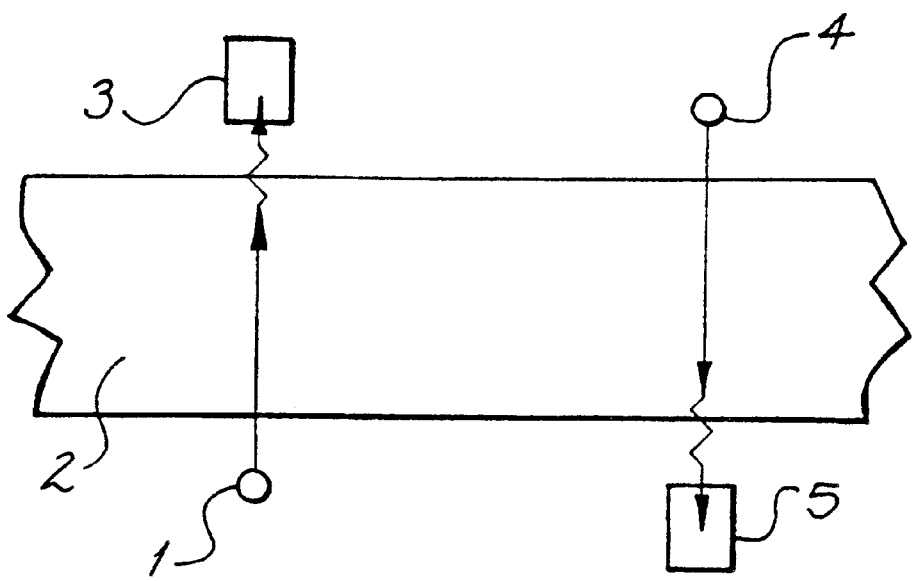
FIG. 1 is a schematic drawing of two transmission gauges.

Examples of such multiple transmission and/or backscattering configurations are as follows:

One neutron source 1 is placed beneath the sample 2 opposite one or more gamma-ray detectors 3 placed above the sample and one neutron source 4 placed above the sample 2 opposite one or more gamma-ray detectors 5 placed beneath the sample, as shown in FIG. 1. The distance between the two source/detector transmission pairs can be selected to optimise the spatial response of the system by balancing contributions from NIS and TNC gamma-rays.

Figure 2:
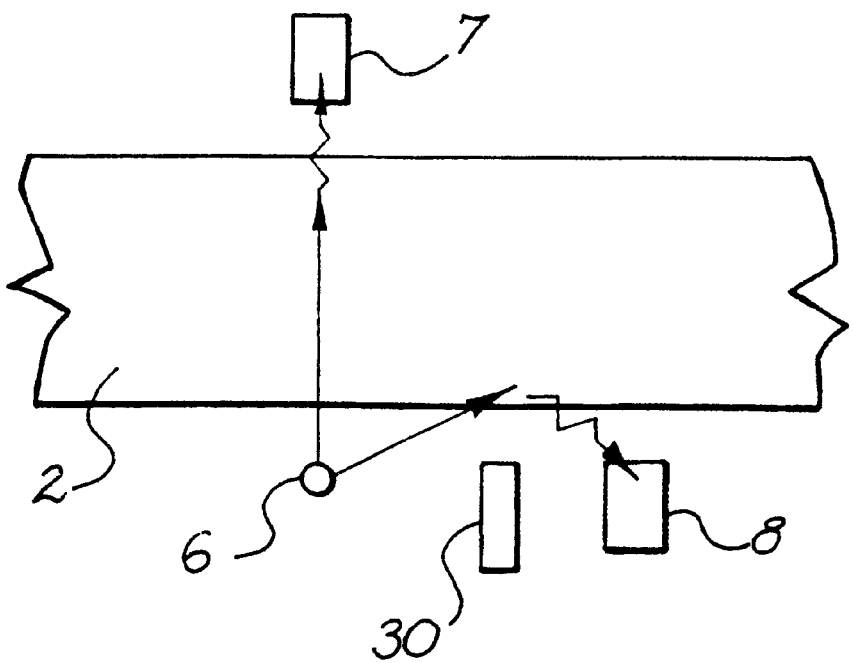
FIG. 2 is a schematic drawing of transmission and backscatter gauges using a single fast neutron source.

One neutron source 6 is placed beneath the sample 2 opposite one or more gamma-ray detectors 7 placed above the sample and one or more gamma-ray detectors 8 placed beneath the sample shielded 30 from direct radiation from the neutron source 6, as shown in FIG. 2.

Figure 3:
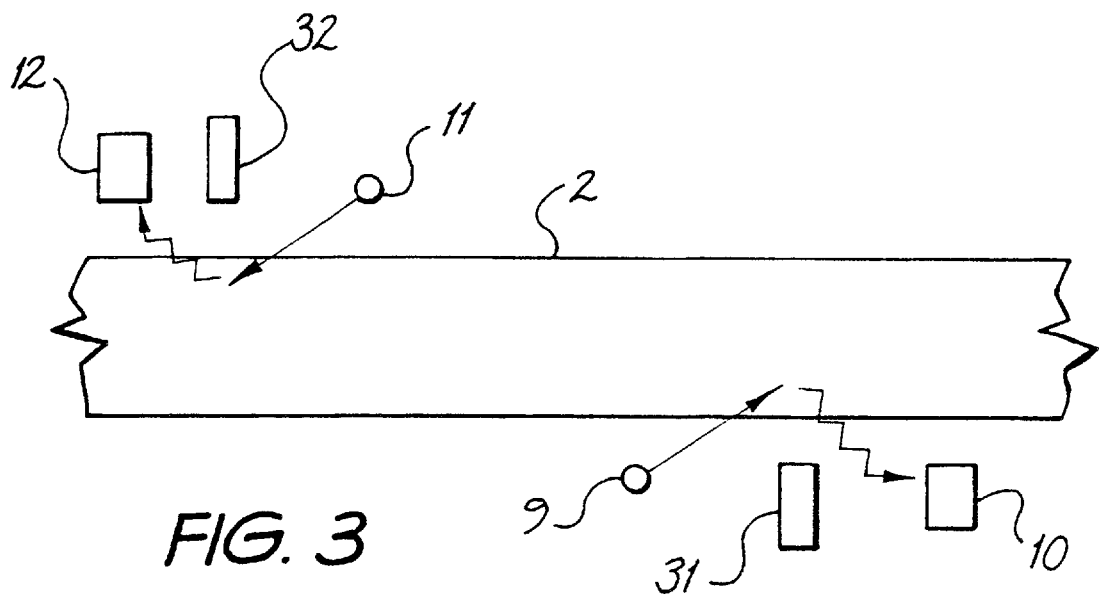
FIG. 3 is a schematic drawing of two backscatter gauges.

One neutron source 9 placed beneath the sample 2 adjacent to and shielded 31 from one or more gamma-ray detectors 10 placed beneath the sample and a second neutron source 11 placed above the sample 2 adjacent to and shielded 32 from one or more gamma-ray detectors 12 placed above the sample 2, as shown in FIG. 3.

Figure 4:
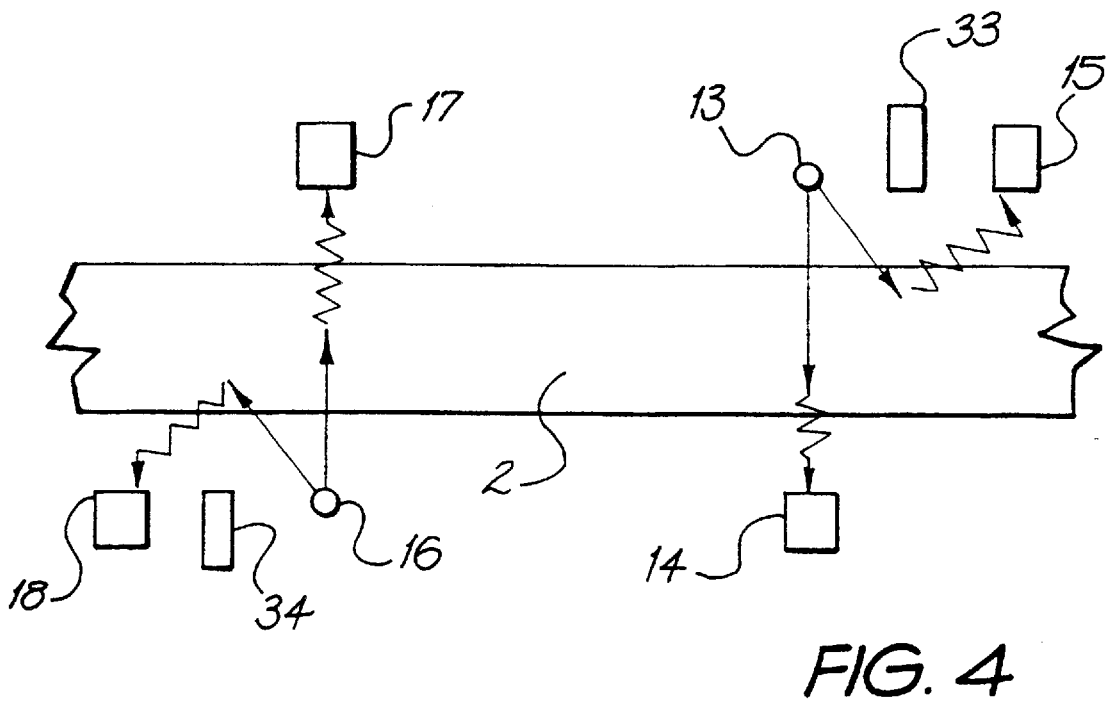
FIG. 4 is a schematic drawing of two transmission and backscatter gauges.
Figure 5A:
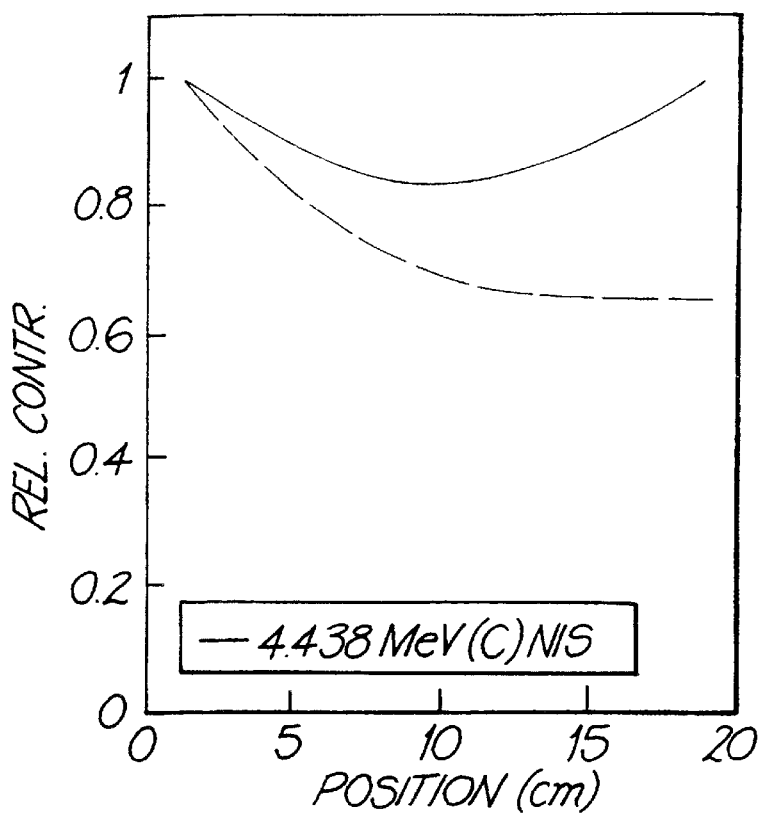
FIG. 5a is a graph showing the results of Monte Carlo calculations of the relative spatial contributions of 4.438 MeV (C) NIS gamma-rays for a 20 cm thick cement raw meal sample, 241Am—Be source(s) and single (dashed) and dual (solid) transmission gauges.
Figure 5B:
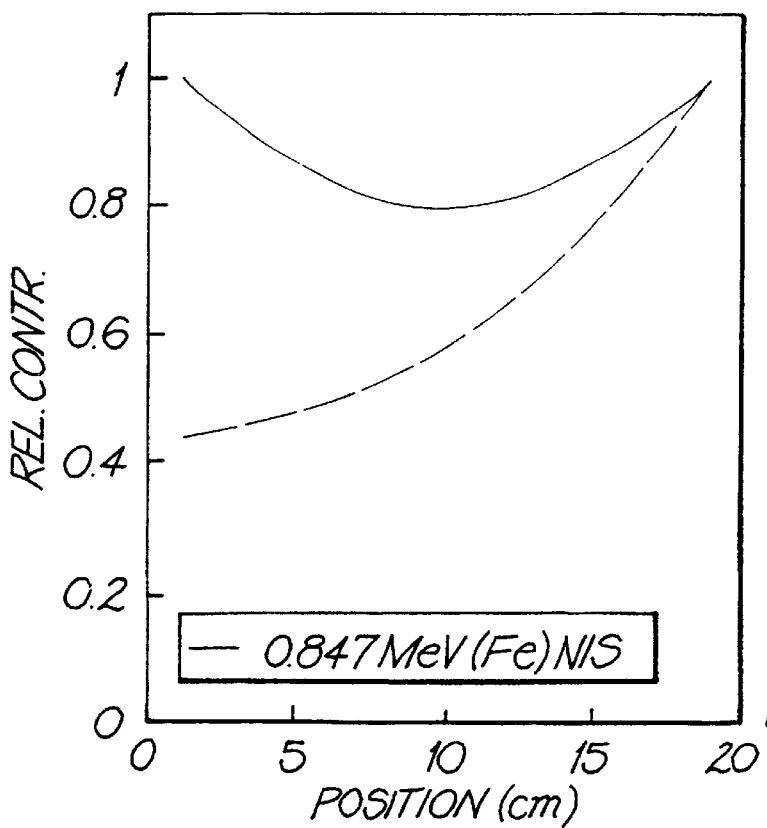
FIG. 5b is a graph showing the results of Monte Carlo calculations of the relative spatial contributions of 0.847 MeV (Fe) NIS gamma-rays for a 20 cm thick cement raw meal sample, 241Am—Be source(s) and single (dashed) and dual (solid) transmission gauges.
Figure 5C:
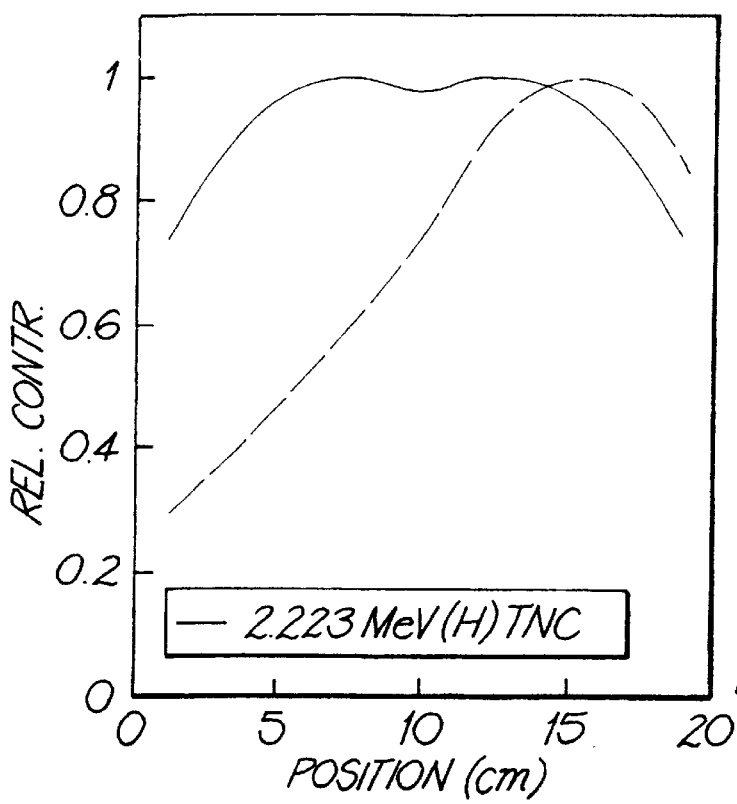
FIG. 5c is a graph showing the results of Monte Carlo calculations of the relative spatial contributions of 2.223 MeV (H) TNC gamma-rays for a 20 cm thick cement raw meal sample, 241Am—Be source(s) and single (dashed) and dual (solid) transmission gauges.
Figure 5D:
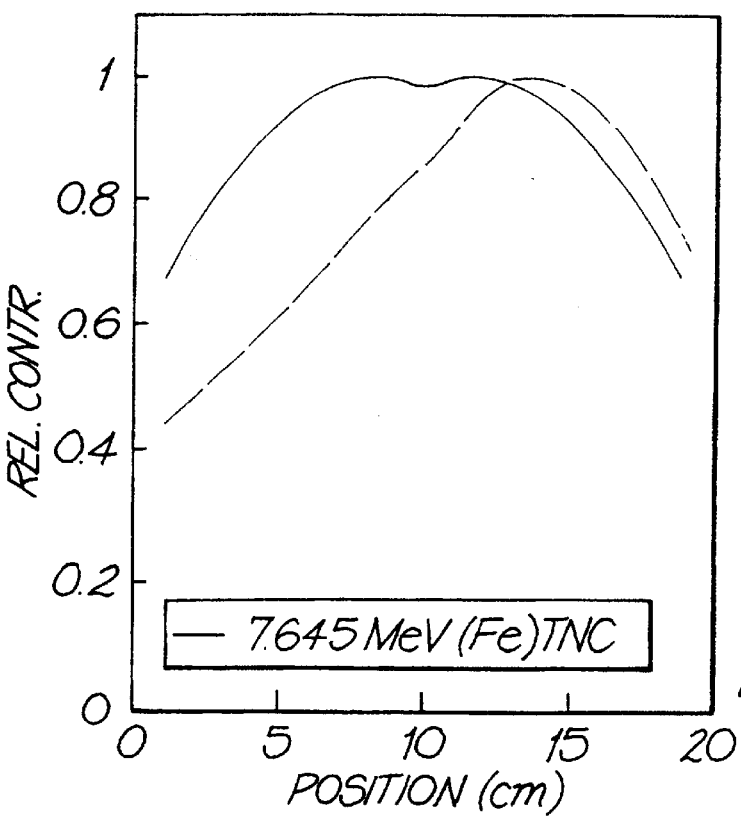
FIG. 5d is a graph showing the results of Monte Carlo calculations of the relative spatial contributions of 7.645 MeV (Fe) NIS gamma-rays for a 20 cm thick cement raw meal sample, 241Am—Be source(s) and single (dashed) and dual (solid) transmission gauges.
Figure 6A:
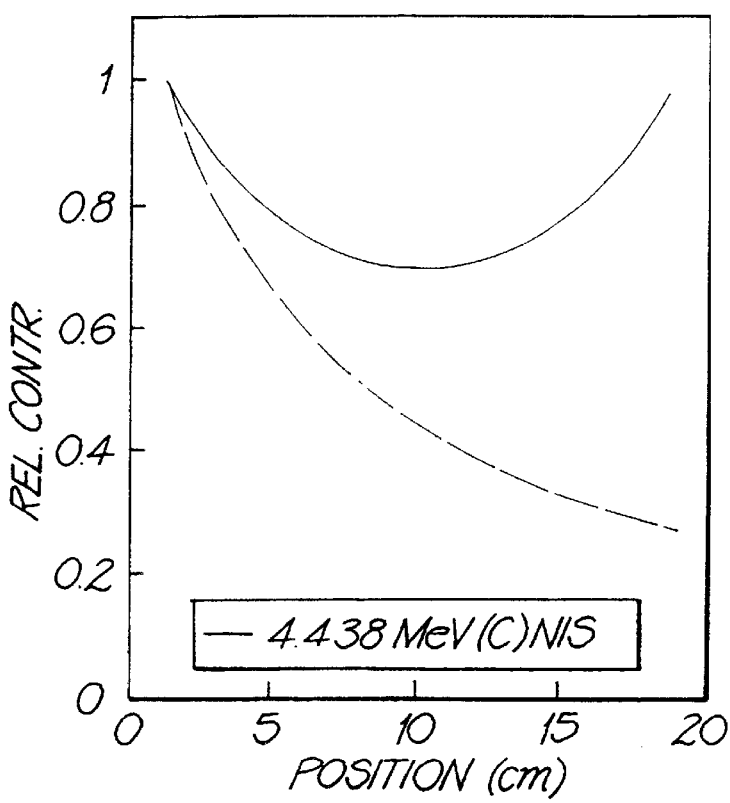
FIG. 6a is a graph showing the results of Monte Carlo calculations of the relative spatial contributions of 4.438 MeV (C) NIS gamma-rays for a 20 cm thick coal sample using 241Am—Be source(s). The dashed line shows the results for a single transmission configuration. The solid line shows the results for dual transmission.
Figure 6B:
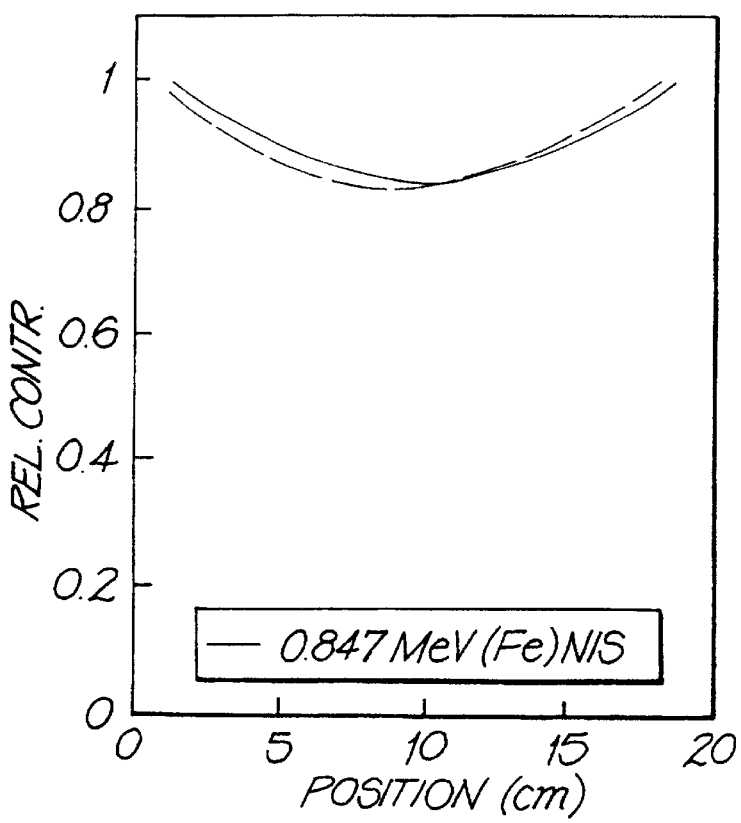
FIG. 6b is a graph showing the results of Monte Carlo calculations of the relative spatial contributions of 0.847 MeV (Fe) NIS gamma-rays for a 20 cm thick coal sample using 241Am—Be source(s) The dashed line shows the results for a single transmission configuration. The solid line shows the results for dual transmission.
Figure 6C:
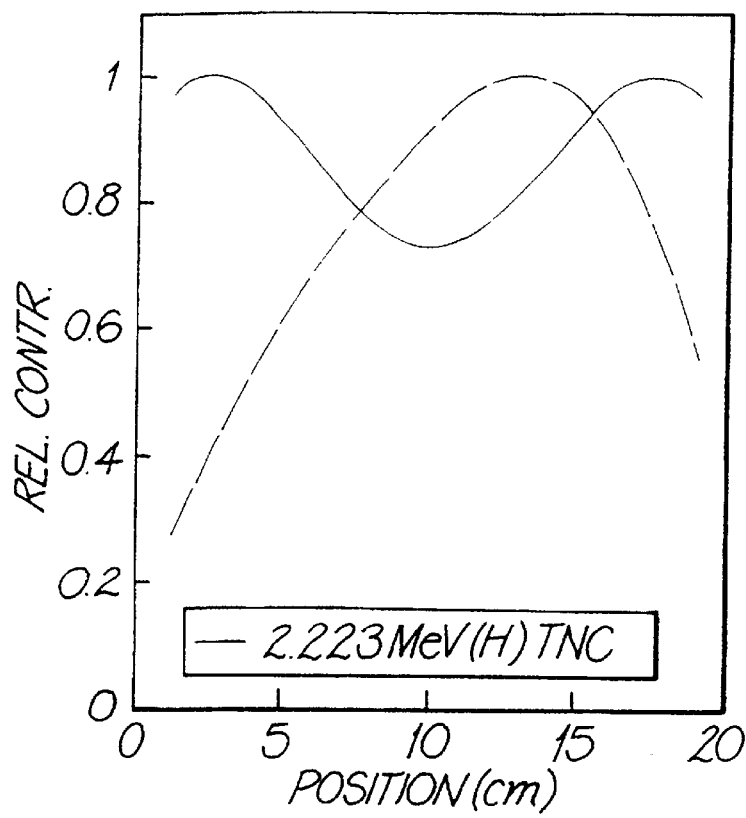
FIG. 6c is a graph showing the results of Monte Carlo calculations of the relative spatial contributions of 2.223 MeV (H) TNC gamma-rays for a 20 cm thick coal sample using 241Am—Be source(s). The dashed line shows the results for a single transmission configuration. The solid line shows the results for dual back-scatter gauges.
Figure 6D:
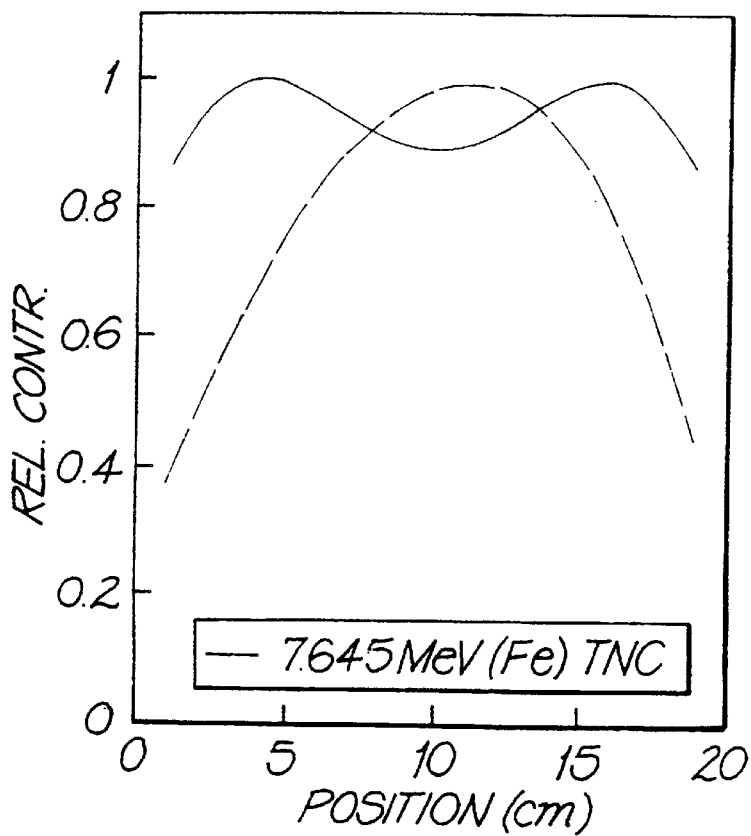
FIG. 6d is a graph showing the results of Monte Carlo calculations of the relative spatial contributions of 7.645 MeV (Fe) TNC gamma-rays for a 20 cm thick coal sample using 241Am—Be source(s). The dashed line shows the results for a single transmission configuration. The solid line shows the results for dual back-scatter gauges.

One neutron source 13 placed above the sample 2 opposite a gamma-ray detector 14 placed beneath the sample and a second detector 15 placed above the sample adjacent to and shielded 33 from the source 13 and a second neutron source 16 placed beneath the sample opposite a gamma-ray detector 17 placed above the sample 2 and a second detector 18 placed beneath the sample 2 adjacent to and shielded 34 from the source 16, as shown in FIG. 4.

Demonstration of Method by Monte Carlo Simulation

A deterministic calculation the rate of gamma-ray production within a sample is not in general possible, due to the complexity of the processes occurring. Instead, a stochastic (Monte Carlo) sampling process can be used to estimate the number of specific gamma-rays produced per source neutron on a regular array of points within the sample. Given the distance of these grid points from the detector and the attenuation length of gamma-rays within the sample, the probability that a gamma-ray reaches the detector without interacting can be evaluated deterministically. Combining these results allows the relative importance of different regions of the sample to the composition measurement to be calculated.

As an example, a simple geometry, including a rectangular slab of sample material, a supporting conveyor belt and a neutron source with appropriate shielding material, has been modelled in a Monte Carlo program. The rate of production of two typical NIS gamma-rays (0.847 MeV iron and 4.438 MeV carbon) and two typical TNC gamma-rays (2.223 MeV hydrogen and 7.645 MeV iron) were determined. These were then multiplied by appropriate gamma-ray attenuation factors to simulate a detector placed in a transmission or backscatter configuration. Multiple source/detector configurations were then constructed from linear combinations of the single source/detector configurations.

FIGS. 5 and 6 show the result of these studies for two typical materials; cement raw meal, which has a low hydrogen content and hence a long neutron attenuation length, and coal which has a higher hydrogen content. In the figures, the relative contribution of the specified gamma-ray has been plotted as a function of depth within the sample. The dashed lines show the results for a single source/single detector transmission configuration, and the solid lines the results for a dual arrangement (either dual transmission or dual backscatter). In all cases, the four possible configuration illustrated in FIGS. 1–4 were evaluated and the one showing the best spatial insensitivity selected. The bias for the single transmission gauge is due to the relative attenuation of neutrons and gamma-rays together with geometrical factors. It can be seen that the dual configurations show considerably improved spatial insensitivity.

Validation of the Monte Carlo Predictions

In order to validate the predictions of the Monte Carlo models, a series of experiments was performed, in which an iron plate was buried at various depths inside a silica sample and the iron gamma-ray contribution measured. The calculated and measured gamma-ray contributions from the iron plate are compared in Table 1. The uncertainties on the results quoted in the 'Experiment' column are approximately 15%. Within this level of error, the Monte Carlo and experimental data are in good agreement.

TABLE 1

Comparison of Monte Carlo simulation and experimental measurement results for gamma-ray production in an iron plate buried inside a silica sample. All columns have been scaled to unity for the 'bottom' position.

| Position of plate inside sample | Number of γ-rays produced in plate | Relative probability of γ-ray reaching detector | Detected γ-rays (Monte Carlo calculation) | Detected γ-rays (Experiment) |
|---|---|---|---|---|
| Bottom | 1.00 | 1.0 | 1.0 | 1.0 |
| Middle | 0.52 | 3.0 | 1.6 | 1.6 |
| Top | 0.20 | 13.5 | 2.7 | 3.2 |

Determination of Optimum Source/Detector Configuration

For the two sample materials studied, the dual transmission configuration yields the optimum spatial insensitivity for NIS gamma-rays. For TNC gamma-rays, the dual transmission configuration performs best for cement, and the dual backscatter configuration best for coal. The preferred geometry for many on-belt cement applications involving both NIS and TNC gamma-rays is therefore the dual transmission configuration. The preferred geometry for many on-belt coal applications involving both NIS and TNC gamma-rays is a combination of the configurations shown in FIGS. 1 and 3 where the distance between the sources and detectors on the same side of the belt is chosen to achieve optimum spatial uniformity by balancing contributions from NIS and TNC gamma-rays.

It is envisaged that for measurement of specific elements within samples of differing composition and thickness, any of the four source/detector configurations illustrated in FIGS. 1–4, or variations thereon as discussed above, may prove optimal. Monte Carlo modeling and supporting experiments can be used to select the best arrangement.

INDUSTRIAL APPLICATIONS

Examples of potential applications are as follows:

The coal industry has an expanding need for on-conveyor belt analysis, particularly for improved product quality control. The requirement is for better analytical accuracy and better availability of on-line gauges. The parameters of most interest to the coal industry are ash, moisture, sulphur and specific energy. Coal consists of combustible coal matter (carbon, hydrogen, oxygen and nitrogen) and mineral matter; ash is the oxidised incombustible residue from the combustion of coal On-line determination of key elements such as iron, silica, alumina, manganese and phosphorus is a key requirement for the improved control of mining, blending and beneficiation in the iron ore industry. Analysis is generally required in real time directly on high tonnage conveyor belts.

On-line quality measurement of cement raw materials is a key requirement for the improved control of cement plants. The primary application to be addressed is the on-conveyor belt analysis of raw meal to control the raw mix composition. Elements of primary importance in this application are calcium, silicon, aluminium and iron.

Previous laboratory and plant work has shown that NIS and TNC techniques are capable of accurately determining the concentrations of a wide range of elements in coal, iron ore and cement raw meal provided the samples being measured are homogeneous.

Figure 7:
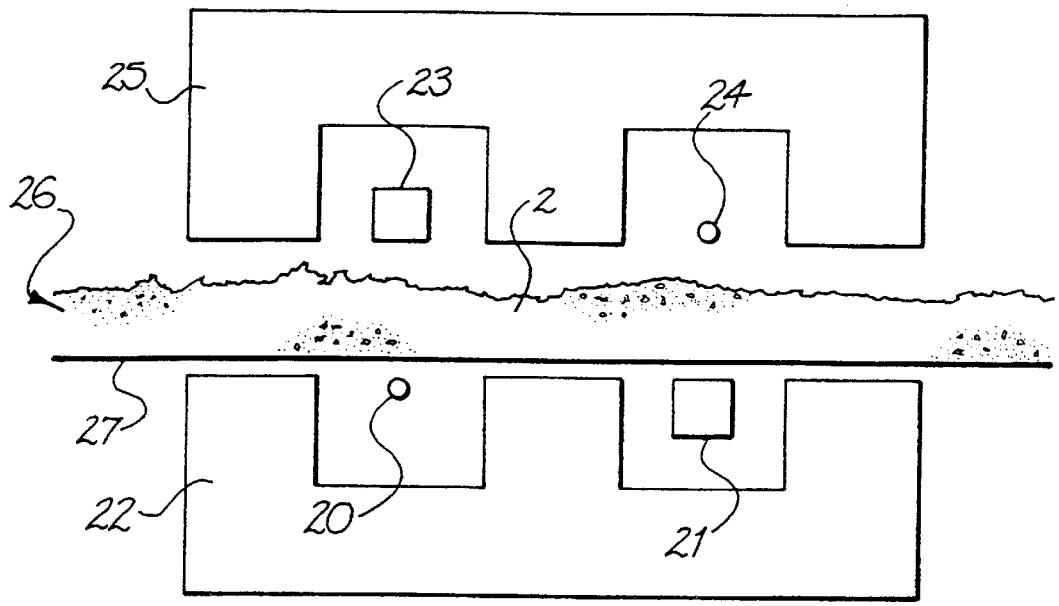
FIG. 7 is a schematic drawing of a practical arrangement of a dual transmission gauge for on-belt sample measurement of cement raw meal samples.

FIG. 7 illustrates a practical arrangement for installation on a conveyor belt using the same geometry as FIG. 1. The arrangement shown in FIG. 7 is the preferred geometry for many on-belt cement applications involving both NIS and TNC gamma-rays. Neutron source 20 and gamma-ray detector 21 are housed in separate compartments of a lower shielded enclosure 22. Gamma-ray detector 23 and neutron source 24 are housed in separate compartments of an upper shielded enclosure 25. A passageway 26 passes between the two shielded enclosures 22 and 25, and a conveyor belt 27 passes through passageway 26 to carry the sample material 2 between the sources and their respective detectors.

Figure 8:
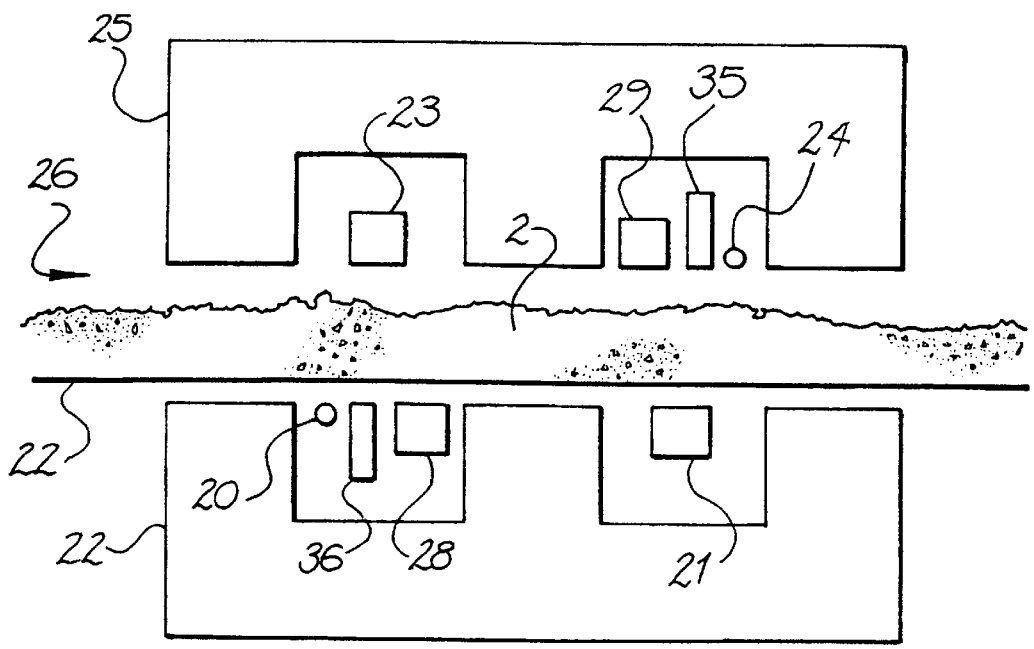
FIG. 8 is a schematic drawing of a practical arrangement of dual transmission/backscatter gauges suitable for the on-line analysis of coal.

FIG. 8 illustrates a practical arrangement for installation on a conveyor belt using the same geometry as FIG. 4 which is suitable for on-belt coal analysis. In this example additional gamma-ray detectors 28 and 29 are included in the compartments with neutron sources 20 and 24 respectively. Gamma-ray detector 28 is shielded 36 from neutron source 20, and gamma-ray detector 29 is shielded 35 from neutron source 24. The additional gamma-ray detectors are arranged to measure backscattered radiation.

It should be understood that the lower and upper shielded enclosures are designed to prevent the escape of undesirable radiation, and not to reduce neutron energies before the neutrons enter the measurement volume.

It will be appreciated by persons skilled in the art that numerous variations and/or modifications may be made to the invention as shown in the specific embodiments without departing from the spirit or scope of the invention as broadly described. For instance, variations where two sources are used and each has an associated transmission and backscatter detector. The present embodiments are, therefore, to be considered in all respects as illustrative and not restrictive.

What is claimed is:

1. A bulk material analyser, including:
    a shielded enclosure defining an analysis zone within it and having a passageway through it to allow transport of bulk material through the analysis zone;
    at least one neutron source and at least two gamma-ray detectors are disposed within the enclosure to measure gamma-rays produced in the bulk material by both the neutron inelastic scatter and thermal neutron capture processes;
    a neutron source and a gamma-ray detector are arranged in either a transmission or backscatter geometry;
    a second gamma-ray detector is arranged either in a transmission or backscatter geometry with or without using a second neutron source;
    the arrangement of the detectors being such that the bias in the spatial response of each, that is caused by the relative attenuation of neutrons and gamma-rays in the bulk material, at least partly compensates for the bias in the spatial response of the other.

2. A bulk material analyser according to claim 1, wherein the shielded enclosure is made of a material which contains a high hydrogen density.

3. A bulk material analyser according to claim 2, wherein the shielded enclosure is made of a material which contains a high hydrogen density in combination with a material of high neutron capture cross section.

4. A bulk material analyser according to claim 3, wherein the material of high neutron capture cross section is boron or lithium.

5. A bulk material analyser according to claim 1, wherein, in use, the bulk material is transported though the analysis zone on a conveyor belt or chute that passes along the passageway.

6. A bulk material analyser according to claim 1, wherein one neutron source is placed beneath the passageway opposite a gamma-ray detector placed above the passageway and one neutron source is placed above the passageway opposite a gamma-ray detector placed beneath the passageway.

7. A bulk material analyser according to claim 1, wherein one neutron source is placed beneath the passageway opposite a gamma-ray detector placed above the passageway and one gamma-ray detector is placed beneath the passageway shielded from direct radiation from the neutron source.

8. A bulk material analyser according to claim 1, wherein one neutron source is placed above the passageway adjacent to and shielded from a gamma-ray detector, and another neutron source is placed below the passageway adjacent to and shielded from another gamma-ray detector.

9. A bulk material analyser according to claim 1, wherein one neutron source is placed above the passageway adjacent to and shielded from a first gamma-ray detector, and a second gamma-ray detector is placed beneath the passageway; and a second neutron source is placed below the passageway adjacent to an shielded from a third gamma-ray detector, and a fourth gamma-ray detector is placed above the passageway.

10. A bulk material analyser according to claim 1, wherein one neutron source is placed above the passageway opposite a gamma-ray detector placed beneath the passageway and a second neutron source is placed beneath the passageway adjacent to and shielded from gamma-ray detector placed beneath the passageway.

11. A bulk material analyser according to claim 1 where the distance between the sources and detectors on the same side of the belt is chosen to achieve optimum spatial uniformity.

12. A bulk material analyser according to claim 1 wherein the neutron sources have sufficient energy to excite NIS gamma-rays from the element of interest.

13. A bulk material analyser according to claim 1, wherein hydrogenous material is provided around the neutron source to reduce the average neutron energy from the source.

14. A bulk material analyser according to claim 1, wherein the neutron source is a radioisotope source, or an RF linac, or a neutron generator in either continuous or pulsed mode.

15. A bulk material analyser according to claim 1, wherein the neutron-induced gamma-ray measurements are combined with separate measurements of gamma-ray transmission, thermal neutron flux or fast neutron flux, or any combination of them.

16. A bulk material analyser according to claim 1, wherein pulses comprising the output from the detectors are amplified by means of a suitable amplifier, and resultant amplified spectra then are processed using a suitable computer to produce an output indicative of the elemental composition of the material passing through the analyser.

17. A bulk material analyser according to claim 1, wherein the analyser utilises a high-energy neutron source such as 241Am—Be, a neutron generator or 252 Cf and scintillation or solid state detectors such as thallium activated sodium iodide (NaI(Tl)), bismuth germanate (BGO) or hyperpure germanium.

18. A bulk material analyser according to claim 1, wherein the NIS measurements are combined with TNC measurements.

19. A bulk material analyser according to claim 1, wherein additional sources are positioned laterally across the passageway on the same side of the passageway as the existing sources.

20. A bulk material analyser according to claim 1, wherein additional gamma-ray detectors are positioned laterally across the passageway on the same side of the passageway as the existing detectors.

21. A bulk material analyser according to claim 1, where uniformity of spatial response of TNC gamma-rays is improved by the use of neutron moderators and reflectors placed around the source and sample.

* * * * *